(12) United States Patent
Plos et al.

(10) Patent No.: US 7,179,304 B2
(45) Date of Patent: Feb. 20, 2007

(54) PROCESS FOR DYEING KERATIN FIBERS WITH AT LEAST ONE POLYCYCLIC AROMATIC VICINAL TRIONE

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 396 days.

(21) Appl. No.: 10/898,266

(22) Filed: Jul. 26, 2004

(65) Prior Publication Data

US 2005/0050652 A1    Mar. 10, 2005

Related U.S. Application Data

(60) Provisional application No. 60/499,377, filed on Sep. 3, 2003.

(30) Foreign Application Priority Data

Jul. 25, 2003 (FR) .................. 03 09172
Mar. 4, 2004 (FR) .................. 04 02246

(51) Int. Cl.
*A61K 7/13* (2006.01)
(52) U.S. Cl. .............. 8/405; 8/406; 8/407; 8/410; 8/411; 8/421; 8/607; 568/327
(58) Field of Classification Search ............ 8/405, 8/406, 407, 410, 411, 421, 607; 568/327
See application file for complete search history.

(56) References Cited

FOREIGN PATENT DOCUMENTS

| DE | 43 17 855 | 12/1994 |
|---|---|---|
| DE | 4317855 A1 * | 12/1994 |
| DE | 43 35 627 A1 | 4/1995 |
| DE | 197 17 222 | 10/1998 |
| DE | 197 45 355 | 4/1999 |
| DE | 198 45 481 | 4/2000 |
| WO | WO 95/11001 | 4/1995 |
| WO | WO 01/97764 A2 | 12/2001 |

OTHER PUBLICATIONS

English Abstract of the Patent No. DE 4317855 A1.*
STIC Search Report (Aug. 7, 2006).*
Database CAPLUS 'Online!, XP002284669, Database accession No. 1989:596731.
Database CAPLUS 'Online!, XP002284670, Database accession No. 1981:14638.
Database CAPLUS 'Online!, XP002284671, Database accession No. 1980:514956.
English language Derwent Abstract of DE 43 35 627 A1, Apr. 20, 1995.
G. Errera, *Ossidazione dell'ossichetoperinaftindenc*, 431 Gzz. Chim. Ital. 583 (1913).
R. Gleiter et al., *Synthesis and Properties of 4,4,9,9-Tetramethyl[12]paracyclophane-5,6,7,8-tetrone*, 57 J. Org. Chem. 252 (1992).

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to the process, for dyeing keratin materials, comprising applying to the keratin materials a composition comprising, in a medium appropriate for dyeing, at least one polycyclic aromatic vicinal trione, which may be optionally combined with at least one compound comprising a liable hydrogen. Further disclosed herein is a cosmetic dyeing composition, a multicomponent hair dye composition, and a multicompartment kit comprising the same.

23 Claims, No Drawings

PROCESS FOR DYEING KERATIN FIBERS WITH AT LEAST ONE POLYCYCLIC AROMATIC VICINAL TRIONE

This application claims benefit of U.S. Provisional Application No. 60/499,377, filed Sep. 3, 2003.

The present disclosure relates to compositions for dyeing keratin materials, such as compositions for hair dyeing, comprising at least one polycyclic aromatic vicinal trione, for example, optionally combined with at least one compound comprising a primary or secondary amine functional group or with at least one compound containing an activated methylene functional group. Further disclosed herein is a method for dyeing using such compositions and a multi-component dyeing kit used for carrying out such a method.

Throughout the years, people have sought to modify the color of their skin, of their eyelashes or of their hair, for instance, to mask grey hair. To do this, several technologies have been developed.

It is known to dye human keratin fibers, such as the hair, with dyeing compositions comprising oxidation dye precursors, generally called oxidation bases. These oxidation bases are colorless or slightly colored compounds which, when combined with oxidizing agents, give rise, through a process of oxidative condensation, to colored compounds. These dyes are insoluble and become trapped inside the hair fiber.

It is also known that one can vary the shades obtained with oxidation bases by combining them with couplers or color modifiers. The variety of molecules used at the level of the oxidation bases and the couplers allows a rich palette of colors to be obtained.

The colors obtained can exhibit good longevity with exposure to shampoo, i.e., color fastness. However, the oxidation reaction occurs with the aid of oxidizing products such as hydrogen peroxide in a basic medium. These oxidizing agents attack the keratin of the hair, which can cause cosmetic and mechanical properties to deteriorate the hair considerably in the event of repeated dyeing.

It is also known to dye human keratin fibers by direct dyeing, which comprises applying to the keratin fibers direct dyes that are colored and dyeing molecules having affinity for the fibers. Examples of direct dyes which are conventionally used include nitro dyes, benzene dyes, anthraquinone dyes, nitropyridine dyes, azo dyes, cationic azo dyes, xanthene dyes, acridine dyes, azine dyes or dyes of the triarylmethane type or natural dyes.

The colors that can thus be obtained are chromatic and do not bring about chemical degradation of keratin; however, they have the disadvantage of being only temporary or semipermanent, e.g., the color can fade after only 4 to 5 shampooings.

A need therefore remains for systems and methods for dyeing which allow good color fastness to be obtained without involving the use of oxidizing agents which are likely to damage keratin materials.

Accordingly, the present disclosure relates to the use of polycyclic aromatic vicinal triones described in greater detail below, which make it possible to dye keratin materials, such as the hair, with color fastness that can be equivalent or even superior to that obtained by oxidation dyeing. This can be accomplished in the absence of strong oxidizing agents, thereby preserving the keratin materials.

The polycyclic aromatic vicinal triones disclosed herein may be used, for example, in combination with compounds comprising a labile hydrogen, such as primary or secondary amines or compounds comprising an activated methylene functional group.

The colors thus obtained can exhibit good chromaticity and can be distinguished, for instance, by their excellent color fastness to washing (several tens of shampooings).

An aspect of the present disclosure, therefore, is the process, for dyeing keratin materials, comprising applying to the keratin materials a composition comprising, in a medium appropriate for dyeing, at least one compound of formula (I) or (II) or its tautomeric form:

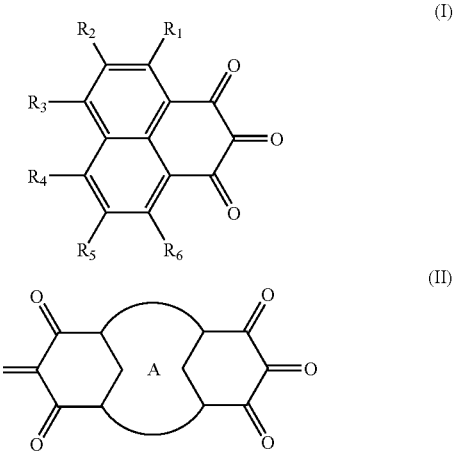

wherein $R^1$, $R^2$, $R^3$, $R^4$, $R^5$ and $R^6$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl) amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy) carbonyl radicals; nitro radicals; sulphonato radicals; tri ($C_{1-6}$ alkyl)ammonio radicals; and aromatic radicals comprising at least 5 members that are monocyclic or polycyclic, comprising fused or non-fused rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl and pyridinyl groups;

alternatively $R^1$ and $R^2$, $R^2$ and $R^3$, $R^3$ and $R^4$, $R^4$ and $R^5$, or $R^5$ and $R^6$ form together, in pairs, an entity chosen from —O—CH$_2$—O— radicals; and aromatic and nonaromatic, 5- and 6-membered ring, optionally containing at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals.

A is chosen from aromatic and aliphatic polycyclic systems optionally comprising at least one heteroatom chosen from N, O, S and P and optionally bearing at least one substituent chosen from the substituents of the aromatic groups represented by $R^1$ to $R^6$ above.

Such compositions are, for instance, useful for dyeing keratin fibers, such as the hair.

In another aspect of the present disclosure, A is chosen so as to form, by condensation with the two $C_6$-trione rings a system containing delocalized π electrons.

The halogen atoms comprise chlorine, bromine, fluorine, and iodine atoms.

The compounds of formulae (I) and (II) also comprise the corresponding addition salts with acids and the addition salts with bases.

The polycyclic aromatic vicinal triones of formulae (I) and (II) above may be used in the present disclosure in a cosmetically acceptable medium which may comprise a large fraction of water. When the compounds are dissolved in such an aqueous medium, these compounds are in hydration equilibrium with the geminal diol form (or carbonyl hydrate) corresponding to the following formulae (Ia) and (IIa):

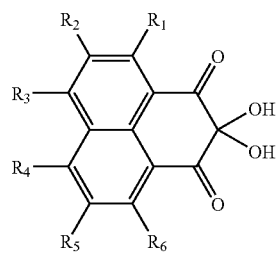

(Ia)

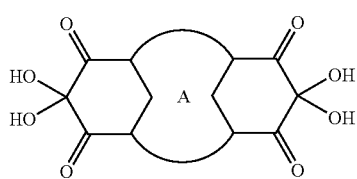

(IIa)

When reference is made, in the present disclosure, to triones of formulae (I) and (II), they consequently comprise not only the compounds of formulae (I) and (II) but also the corresponding hydrated forms of formulae (Ia) and (IIa).

In a further aspect of the compounds of formula (II), A is chosen from a naphthalene ring that forms, by condensation with the two adjacent $C_6$ rings, a pyrene-1,2,3,6,7,8-hexone of formula (III):

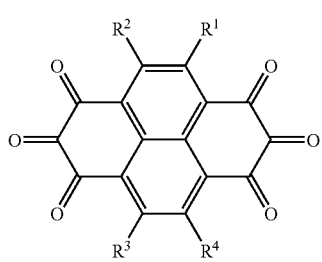

(III)

wherein the substituents $R^1$ to $R^4$ have the definitions indicated above for $R^1$ to $R^6$.

In still another embodiment of the compounds of formula (II), A is chosen from a perylene rig that forms, by condensation with the two adjacent $C_6$ rings, a dibenzo[cd,lm]perylene-1,2,3,8,9,10-hexone of formula (IV):

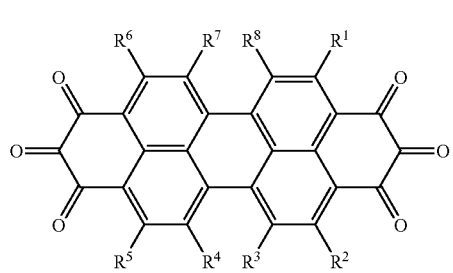

(IV)

wherein the subsittuents $R^1$ to $R^8$ have the meaning indicated above for the substituents $R^1$ to $R^6$.

Non-limiting examples of fused-rings comprising polycyclic aromatic vicinal triones that can be used in accordance with the present disclosure for dyeing hair fibers are the following:

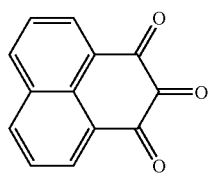

(a)

1H-phenalene-1,2,3-trione

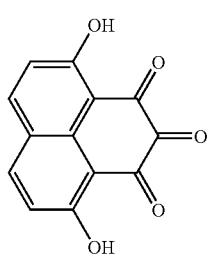

(b)

4,9-dihydroxy-1H-phenalene-1,2,3-trione

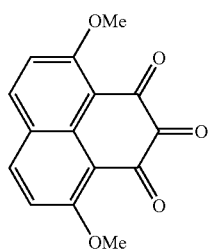

(c)

4,9-dimethoxy-1H-phenalene-1,2,3-trione

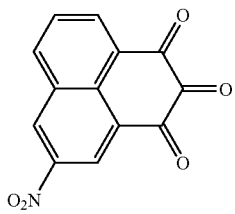

5-nitro-1H-phenalene-1,2,3-trione

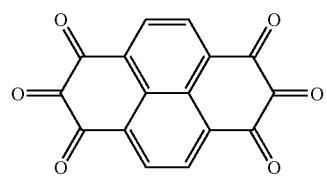

1,2,3,6,7,8-pyrenehexone

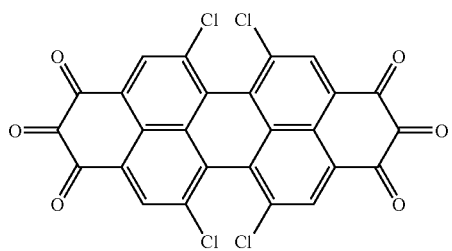

5,6,12,13-tetrachloro-dibenzo[cd,lm]perylene-1,2,3,8,9,10-hexone

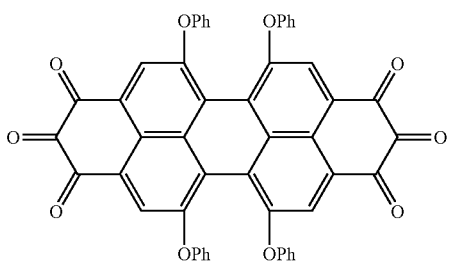

5,6,12,13-tetraphenoxy-dibenzo[cd,lm]perylene-1,2,3,8,9,10-hexone

The polycyclic aromatic vicinal triones of formulae (I) and (II) as disclosed herein are known. The synthesis of the above ninhydrin derivatives (a) to (g) (i.e., compounds of formulae (I) and (II)) is described in the following two publications:

1H-phenalene-1,2,3-trione: G. Errera Gazz. Chim. Ital. 431, 583 (1913); and 1,2,3,6,7,8-pyrenehexone: R. Gleiter, R. Kraemer, H. Irngartinger, C. Bissinger, J. Org. Chem. 57, 252 (1992).

In accordance with the present discisoure, the polycylic aromatic vicinal triones of formulae (I) and (II) described above may be used alone for dyeing keratin materials. For example, these compounds are capable of generating colored molecules with the amine functional groups of keratin (i.e., colored reaction).

It may also be possible to use the at least one compound of formula (I) and/or (II) together with at least one activator that makes it possible to modify the kinetics of reaction of the ninhydrin compound with the keratinous material. Such an activator may be chosen from oxidizing agents, reducing agents, Brönsted acids, metal catalysts such as catalysts based on a transition metal such as iron, platinum and palladium, proteins, for instance, one or more enzymes, compounds which modify the ionic strength of the medium, such as NaCl salts, compounds comprising a labile hydrogen chosen from compounds comprising a primary or secondary amine functional groups and compounds comprising an activated methylene functional groups. It is, of course, also possible to use a mixture of such compounds.

For example, the compounds with primary amine or secondary amine functional groups may be aromatic amines.

Non-limiting examples of aromatic amines that may be mentioned include: N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, dibromohydrate of 2,5-dihydroxy-4-morpholinoaniline, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino-, 3-amino or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraamino-benzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino- 4-hydroxypyrocatechol, and aromatic anilines and aromatic phenols comprising another aromatic residue, of formula (II)

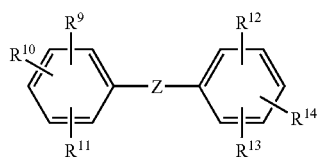

(II)

wherein $R^9$ is chosen from hydroxyl and amino radicals optionally substituted with $C_{1-4}$ alkyl, $C_{1-4}$ hydroxyalkyl, and ($C_{1-4}$ alkoxy)-($C_{1-4}$ alkyl) radicals, $R^{10}$, $R^{11}$, $R^{12}$, $R^{13}$ and $R^{14}$, which may be identical or different, are chosen from hydrogen atoms, hydroxyl, carboxylic, sulphonic and amino radicals, optionally substituted with a radical chosen from $C_{1-4}$ alkyl, $C_{1-4}$ hydroxyalkyl, and ($C_{1-4}$ alkoxy)-($C_{1-4}$ alkyl) radicals, Z is chosen from a direct bond; a $C_{1-4}$ hydrocarbon radical that may be saturated or unsaturated, optionally hydroxylated; carbonyl radicals; sulphonyl radicals; imino radicals; oxygen atoms; and sulphur atoms; and radicals of formula $Q$—$(CH_2$—$P$—$CH_2$—$Q')_o$ wherein "o" is a number between 1 and 4, P is chosen from a direct bond and —$CH_2$— and —CHOH— radicals, Q and Q', which may be identical or different, are chosen from oxygen atoms, $NR^{15}$ radicals wherein $R^{15}$ is chosen from a hydrogen atom, $C_{1-4}$ alkyl, $C_{1-4}$ hydroxyalkyl, O—$(CH_2)_p$NH, and NH—$(CH_2)_{p'}$—O radicals wherein p and p' are chosen from 2 or 3.

The nonaromatic primary or secondary amines may be chosen from at least one, for example, 2-aminoethanol, 2-methoxyethylamine, 2-ethoxyethylamine, 2-(2-aminoethoxy)ethanol, 2- or 3-aminopropanol, 2,3-dihydroxypropylamine, 4-hydroxypropyl-amine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines such as glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

The compounds comprising an activated methylene functional group may be chosen from at least one, for example, 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone, and 1-methyl-3-phenyl-2-pyrazolinone.

Some primary and secondary amines, and some compounds comprising activated methylene functional groups, and other compounds comprising a labile hydrogen are also described in German Patent Application Nos. DE 43 17 855, DE 197 17 222, DE 198 45 481, and DE 197 45 355 wherein the compounds are used for dyeing keratin fibers in combination with ninhydrin derivatives.

When the polycyclic aromatic vicinal triones of formulae (I) and (II) are used in combination with a primary or secondary amine or with a compound comprising an activated methylene functional group, it is necessary to store these different reagents separately in order to avoid a premature color reaction. The reagents are only brought into contact immediately before application to the hair by freshly mixing two compositions comprising the vicinal triones of formulae (I) and (II) and the primary or secondary amine and/or the compound comprising an activated methylene functional group, respectively.

Another aspect of the present disclosure is a multicomponent ready-to-use dyeing composition comprising
at least one first component comprising a composition comprising at least one polycyclic aromatic vicinal trione of formula (I) or (II), and
at least one second component comprising a composition comprising at least one compound chosen from compounds comprising primary or secondary amine radicals and compounds comprising an activated methylene functional group, as described above.

This multicomponent ready-to-use dyeing composition may be provided, for example, in the form of a multicompartment kit, with at least one compartment comprising the at least one first component and at least a second compartment comprising the at least one second component.

Yet another aspect of the present disclosure is a cosmetic dyeing composition comprising at least one polycyclic aromatic vicinal trione of formula (I) or (II) and at least one cosmetic active ingredient.

The at least one cosmetic active ingredient that may be present in the cosmetic compositions of the present disclosure is chosen, for example, from vitamins, saccharides, oligosaccharides, polysaccharides which are hydrolyzed and optionally modified, amino acids, oligopeptides, peptides, proteins which are optionally hydrolyzed and optionally modified, polyamino acids, enzymes, fatty acids that are optionally branched, alcohols that are optionally branched, animal waxes, vegetable waxes, mineral waxes, ceramides, pseudoceramides, hydroxylated organic acids, UV-screening agents, antioxidants, anti-free-radical agents, chelating agents, antidandruff agents, seborrhoea-regulating agents, smoothing agents, cationic surfactants, anionic surfactants, nonionic surfactants, amphoteric surfactants, cationic polymers, anionic polymers, neutral polymers, amphoteric polymers, silicones that are optionally organomodified, mineral oils, vegetable oils, animal oils, polyisobutenes, poly($\alpha$-olefins), fatty esters, anionic polymers in dissolved or dispersed form, nonionic polymers in dissolved or dispersed form, reducing agents, solvents, hair dyes such as direct dyes and oxidation dye precursors (bases and/or couplers) different from the claimed compounds comprising primary and secondary amine functional groups, oxidants such as hydrogen peroxide optionally combined with persalts, pigments and mixtures thereof.

The at least one cosmetic active ingredient, when present, may, for example, be present in an amount ranging from 0.001 to 50% by weight, for instance, from 0.01 to 20% by weight, such as in an amount ranging from 0.1 to 10% by weight, relative to the total weight of the cosmetic composition.

In one embodiment of the cosmetic dyeing composition according to the present disclosure, the cosmetic active ingredient is at least one ingredient chosen from surfactants and a polymeric agents (polymers), it being possible for these agents to be of a nonionic, cationic, anionic, or amphoteric nature.

As disclosed herein, the hair dyeing compositions used according to the present disclosure are stable during storage when they comprise, as sole dyeing reagents, at least one polycyclic aromatic vicinal trione of formula (I) or (II) but the compositions must be prepared immediately before use when they comprise both at least one polycyclic aromatic vicinal trione of formula (I) or (II) and at least one compound comprising a labile hydrogen, such as primary and secondary amines, or compounds comprising an activated methylene functional group.

These ready-to-use dyeing compositions, whether they are stable during storage or prepared immediately before use, may have a pH, for example, ranging from 2 to 12, for instance, from 3 to 11.

The at least one polycyclic aromatic vicinal trione of formula (I) or (II) may be, for example, present in an amount ranging from 0.0001% to 30% by weight, relative to the total weight of the composition.

The compounds comprising a labile hydrogen which are used in combination with the at least one trione of formula (I) or (II), may be present, for instance, in an amount ranging from 0.0001% to 30%, relative to the total weight of the composition.

Still another aspect of the present disclosure is a process for hair dyeing comprising applying, to the hair, a ready-to-use hair dyeing composition as described above. This composition is left in contact with the hair fibers for a time sufficient to obtain the desired color. This leave-in time can range from 5 minutes to 1 hour, such as 15 to 30 minutes. The colored reaction between the at least one polycylic aromatic vicinal trione and the amine functional groups of the keratin or the compounds comprising a labile hydrogen which may be present, may be accelerated by heating hair impregnated with the dyeing composition. The heating temperature can be less than or equal 80° C., such as less than or equal to 60° C.

After obtaining the desired color, the hair is rinsed and washed.

When compounds comprising a labile hydrogen such as primary or secondary amines or compounds comprising an activated methylene functional group are used, the application of the reagents taking part in the colored reaction may also be performed in two stages, in other words, it is possible to successively apply, in any order, two different compositions one comprising at least one polycyclic aromatic vicinal trione of formula (I) or (II) and the other comprising at least one of a compound comprising a primary or secondary amine functional group and a compound comprising activated methylene functional group.

Still anther aspect of the present disclosure is a two-stage dyeing process comprising applying, to the hair, one after the other, in any order, a composition comprising at least one polycyclic aromatic vicinal trione of formula (I) or (II), and a composition comprising at least one compound comprising a primary or secondary amine functional group, or an activated methylene functional group as deined above for the multicomponent ready-to-use dyeing agent.

This separate application of the two reactive compositions has the advantage of avoiding the handling of colored compositions and thus reduces the risks of staining materials such as clothing.

Satisfactory hair colors can also be obtained when an intermediate rinsing stage is preformed between the application of the first composition and the application of the second composition.

In a similar manner to that described above, hair impregnated with either one of the two components of the multicomponent dyeing process may be heated, for example, to a temperature of less than or equal to 80° C., such as to a temperature less than or equal to 60° C., such heating making it possible to accelerate the colored reaction and to shorten the leave-in time.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The following example is intended to illustrate the invention in a non-limiting manner.

EXAMPLE

The following composition was prepared:

| | |
|---|---|
| 1-H-phenalene-1,2,3-trione (compound of example (a)) | $10^{-2}$ moles |
| Ethanol | 50 g |
| NaOH | qs pH 7 |
| Distilled water | qs 100 g |

The composition was applied to two locks of natural and permanently waved hair which was 90% white, of 1 g each. The bath ratio was 5, the leave-in time was 30 minutes and the temperature was 60° C. At the end of the leave-in time, the locks were rinsed and then washed with a standard shampoo.

The color intensity was evaluated by colorimetry according to the CIELAB system using a Minolta CM3600d colorimeter (illuminant D65, angle of observation: 10°, specular component included).

The CIELAB scoring system defines a calorimetric space in which each color is defined by three parameters ($L^*$, $a^*$ and $b^*$):

the parameter $L^*$ reflects the clarity of the color, the value of $L^*$ being equal to 0 for black and equal to 1 for absolute white; thus, the higher the value of $L^*$, the less intense the color, the parameter $a^*$ corresponds to the axis of the green-red antagonist pair and the parameter $b^*$ to the axis of the blue-yellow antagonist pair.

The table below shows the parameters $L^*$, $a^*$ and $b^*$ of the locks of natural hair and of the permanently waved hair before and after the increase in the color, as $\Delta E$ defined by the equation below:

$$\Delta E = \sqrt{(L^*_{final} - L^*_{initial})^2 + (a^*_{final} - a^*_{initial})^2 + (b^*_{final} - b^*_{initial})^2}$$

ΔE reflects the overall variation in color. The higher the variation in color, the higher its value.

| Hair | | L* | a* | b* | ΔE | Color |
|---|---|---|---|---|---|---|
| Natural | Before dyeing | 60.84 | 0.03 | 11.63 | — | — |
| Natural | After dyeing | 25.71 | −2.45 | 6.54 | 35.58 | matt |
| Permanently waved | Before dyeing | 61.78 | 0.33 | 12.74 | — | — |
| Permanently waved | After dyeing | 18.93 | −0.14 | 2.33 | 4.11 | matt |

What is claimed is:

1. A process for dyeing keratin materials, comprising applying to the keratin materials a composition comprising, in a medium appropriate for dyeing, at least one polycyclic aromatic vicinal trione of formula (I) or (II):

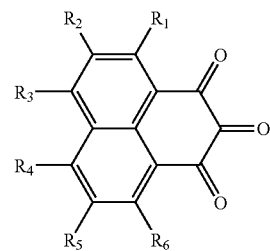

wherein
$R^1$, $R^2$, $R^3$, $R^4$, $R^5$ and $R^6$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy) carbonyl, nitro, sulphonato, tri($C_{1-6}$ alkyl)ammonio, phenoxy, imidazolyl and pyridinyl radicals;

alternatively, $R^1$ and $R^2$, $R^2$ and $R^3$, $R^3$ and $R^4$, $R^4$ and $R^5$, or $R^5$ and $R^6$ form together, in pairs, an entity chosen from —O—CH$_2$—O— radicals; and aromatic and non-aromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals, and A is chosen from aromatic and aliphatic polycyclic systems optionally comprising at least one heteroatom chosen from N, O, S and P and optionally bearing at least one substituent chosen from halogen atoms, and $C_{1-6}$ alkyl, hydroxyl, $C_{1-6}$ alkoxy, amino, mono- and di($C_{1-6}$ alkyl)amino, mono- and di($C_{1-6}$ hydroxyalkyl) amino, thio, $C_{1-6}$ alkylthio, $C_{1-6}$ thioalkyl, ($C_{1-6}$ alkyl) carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl, and pyridinyl radicals.

2. The process according to claim 1, wherein when A is chosen from a naphthalene ring that forms, by condensation with the two adjacent $C_6$ rings, a pyrene-1,2,3,6,7,8-hexone of formula (III):

wherein the substituents $R^1$, $R^2$, $R^3$ and $R^4$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl) amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy) carbonyl, nitro, sulphonato, tri($C_{1-6}$ alkyl)ammonio, phenoxy, imidazolyl and pyridinyl radicals, alternatively, $R^1$ and $R^2$, or $R^3$ and $R^4$, form together, in pairs, an entity chosen from —O—CH$_2$—O— radicals; and aromatic and nonaromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)-carbonyl, nitro, sulphonato, tri($C_{1-6}$ alkyl)ammonio, imidazolyl, and pyridinyl radicals.

3. The process according to claim 1, wherein A is chosen from a perylene ring that forms, by condensation with the two adjacent $C_6$ rings, a dibenzo[cd,lm]perylene-1,2,3,8,9,10-hexone of formula (IV):

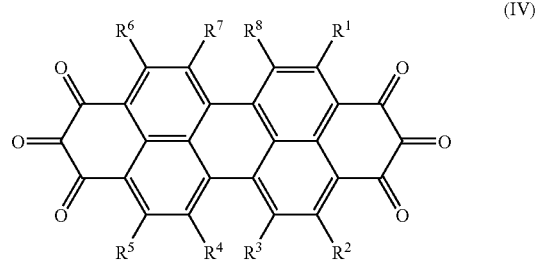

wherein the substituents $R^1$, $R^2$, $R^3$, $R^4$, $R^5$, $R^6$, $R^7$ and $R^8$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl) amino radicals; mono- and di($C_{1-6}$ hydroxyalkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl and pyridinyl radicals, alternatively, $R^1$ and $R^8$, $R^2$ and $R^3$, $R^3$ and $R^4$, $R^4$ and $R^5$, $R^6$ and $R^7$, or $R^7$ and $R^8$ form together, in pairs, an entity chosen from —O—CH$_2$—O— radicals; and aromatic and nonaromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl) amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy) carbonyl, nitro, sulphonato, tri($C_{1-6}$ alkyl)ammonio, imidazolyl, and pyridinyl radicals.

4. The process according to claim 1, wherein the composition further comprises at least one activator that makes it possible to modify the kinetics of the reaction of the at least one polycyclic aromatic vicinal trione of formula (I) or (II) with the keratinous material.

5. The process according to claim 4, wherein the at least one activator is chosen from oxidizing agents, reducing agents, Brönsted acids, metal catalysts, proteins, compounds that modify the ionic strength of the medium, and compounds comprising a labile hydrogen chosen from compounds comprising a primary or secondary amine functional group and compounds comprising an activated methylene functional group.

6. The process according to claim 5, wherein the compound comprising a primary or secondary amine functional group is an aromatic amine chosen from N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-, 2,4- and 2,5-dichloro-p-phenylenediamine, 2-chloro-p-phenylenediamine, dibromohydrate of 2,5-dihydroxy-4-morpholinoaniline, 2-, 3- and 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino-4-hydroxybenzoic acid, 4-amino-3-hydroxybenzoic acid, 2-amino-, 3-amino and 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxy-naphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraamino-benzene, 2,4,5-triaminophenol, pentaaminobenzene, hexaaminobenzene, 2,4,6-triamino-resorcinol, 4,5-diaminopyrocatechol, 4,6-diaminopyrogallol, 3,5-diamino- 4-hydroxy-pyrocatechol, and aromatic anilines and aromatic phenols comprising another aromatic residue of formula (II):

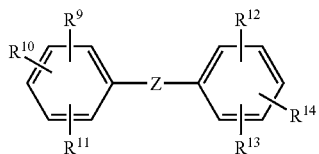
(II)

wherein
- $R^9$ is chosen from hydroxyl and amino radicals optionally substituted with a radical chosen from $C_{1-4}$ alkyl, $C_{1-4}$ hydroxyalkyl, and $(C_{1-4}$ alkoxy)-$(C_{1-4}$ alkyl) radicals,
- $R^{10}$, $R^{11}$, $R^{12}$, $R^{13}$ and $R^{14}$, which may be identical or different, are chosen from hydroxyl and amino radicals, optionally substituted with a radical chosen from $C_{1-4}$ alkyl, $C_{1-4}$ hydroxyalkyl, $(C_{1-4}$ alkoxy)-$(C_{1-4}$ alkyl), carboxylic, and sulphonic acid radicals, and
- Z is chosen from a direct bond; a $C_{1-4}$ hydrocarbon radical that may be saturated or unsaturated and optionally hydroxylated; carbonyl radicals; sulphonyl radicals; imino radicals; oxygen atoms; sulphur atoms; and radicals of formula Q-$(CH_2$—P—$CH_2$-Q')$_o$ wherein "o" is a number ranging from 1 to 4, P is chosen from a direct bond and —$CH_2$— and —CHOH— radicals, Q and Q', which may be identical or different, are chosen from oxygen atoms, $NR^{15}$ radicals wherein $R^{15}$ is chosen from a hydrogen atom, $C_{1-4}$ alkyl, $C_{1-4}$ hydroxyalkyl, O—$(CH_2)_p$NH, and NH—$(CH_2)_{p'}$—O radicals wherein p and p' are equal to 2 or 3.

7. The process according to claim 5, wherein the at least one compound comprising a primary or secondary amine functional group is a nonaromatic amine chosen from 2-aminoethanol, 2-methoxyethylamine, 2-ethoxyethylamine, 2-(2-aminoethoxy)ethanol, 2-aminopropanol, 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines, glucamine, D-glucosamine, D-galactosamine, 1,2-diaminoethane, 1,2-diaminopropane, 1,3-diaminopropane, 1,3-diamino-2-propanol, 2-(2-aminoethylamino)ethylamine, 2-(2-aminoethylamino)ethanol, 3-(2-aminoethylamino)-propylamine, and 3-(2-aminoethylamino)propanol.

8. The process according to claim 5, wherein the compound comprising an activated methylene functional group is chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethyl-benzothiazolium iodide, 2,3-dimethylbenzothiazolium p-toluenesulphonate, rhodanine, rhodanine acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone, and 1-methyl-3-phenyl-2-pyrazinone.

9. The process according to claim 1, wherein the composition has a pH ranging from 2 to 12.

10. The process according to claim 1, wherein the composition has a pH ranging from 3 to 11.

11. The process according to claim 1, wherein the at least one polycyclic aromatic vicinal trione of formula (I) or (II) is present in an amount ranging from 0.0001% to 30%, relative to the total weight of the composition.

12. The process according to claim 1, wherein the composition further comprises at least one agent chosen from non-ionic, cationic, anionic and amphoteric surfactants, and non-ionic, cationic, anionic and amphoteric polymers.

13. A cosmetic composition for dyeing keratin material comprising, in a cosmetically acceptable medium,
- at least one agent chosen from non-ionic, cationic, anionic and amphoteric surfactants, and from nonionic, cationic, anionic and amphoteric polymers, and
- at least one polycyclic aromatic vicinal trione of formula (I) or (II):

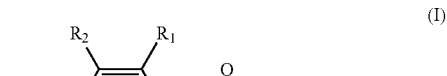

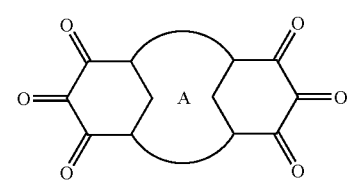

wherein
$R^1$, $R^2$, $R^3$, $R^4$, $R^5$ and $R^6$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl) amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy) carbonyl, nitro, sulphonato, tri($C_{1-6}$ alkyl)ammonio, phenoxy, imidazolyl and pyridinyl radicals;

alternatively, $R^1$ and $R^2$, $R^2$ and $R^3$, $R^3$ and $R^4$, $R^4$ and $R^5$, or $R^5$ and $R^6$ form together, in pairs, an entity chosen from —O—$CH_2$—O— radicals; and aromatic and non-aromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals, and A is chosen from aromatic and aliphatic polycyclic systems optionally comprising at least one heteroatom chosen from N, O, S and P and optionally bearing at least one substituent chosen from halogen atoms, and $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl, and pyridinyl radicals.

14. A ready-to-use cosmetic dyeing composition comprising, in a cosmetically acceptable medium, at least one polycyclic aromatic vicinal trione of formula (I) or (II):

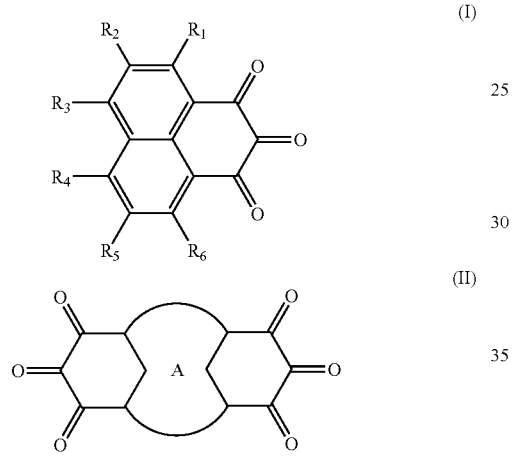

wherein $R^1$, $R^2$, $R^3$, $R^4$, $R^5$ and $R^6$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl) amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy) carbonyl, nitro, sulphonato, tri($C_{1-6}$ alkyl)ammonio, phenoxy, imidazolyl and pyridinyl radicals;

alternatively, $R^1$ and $R^2$, $R^2$ and $R^3$, $R^3$ and $R^4$, $R^4$ and $R^5$, or $R^5$ and $R^6$ form together, in pairs, an entity chosen from —O—$CH_2$—O— radicals; and aromatic and non-aromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals; and A is chosen from aromatic and aliphatic polycyclic systems optionally comprising at least one heteroatom chosen from N, O, S and P and optionally bearing at least one substituent chosen from halogen atoms, and $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl, and pyridinyl radicals, and at least one compound chosen from compounds comprising a primary or secondary amine functional group and compounds comprising an activated methylene functional group, wherein the ready-to-use composition is prepared at the time of use.

15. A multicomponent ready-to-use dyeing composition for keratin material comprising at least one first component comprising a composition comprising, in a medium appropriate for dyeing, at least one polycyclic aromatic vicinal trione of formula (I) or (II):

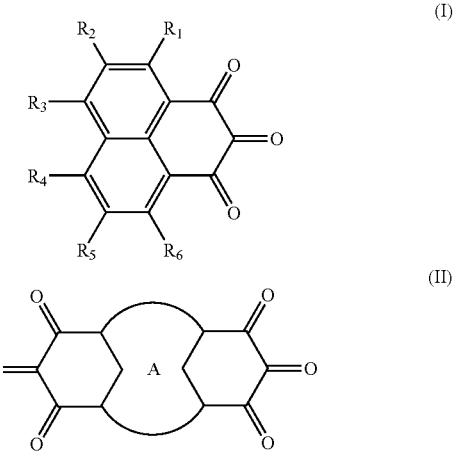

wherein $R^1$, $R^2$, $R^3$, $R^4$, $R^5$ and $R^6$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl and pyridinyl radicals;

alternatively, $R^1$ and $R^2$, $R^2$ and $R^3$, $R^3$ and $R^4$, $R^4$ and $R^5$, or $R^5$ and $R^6$ form together, in pairs, an entity chosen from —O—CH$_2$—O— radicals; and aromatic and non-aromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals, and A is chosen from aromatic and aliphatic polycyclic systems optionally comprising at least one heteroatom chosen from N, O, S and P and optionally bearing at least one substituent chosen from halogen atoms, and $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl, and pyridinyl radicals, and at least one second component comprising at least one activator that makes it possible to modify the kinetics of the reaction of the at least one polycyclic aromatic vicinal trione of formula (I) or (II) with the keratin material.

16. A multicompartment kit for dyeing keratin fibers comprising, at least one first compartment comprising at least one first composition comprising at least one polycyclic aromatic vicinal trione of formula (I) or (II):

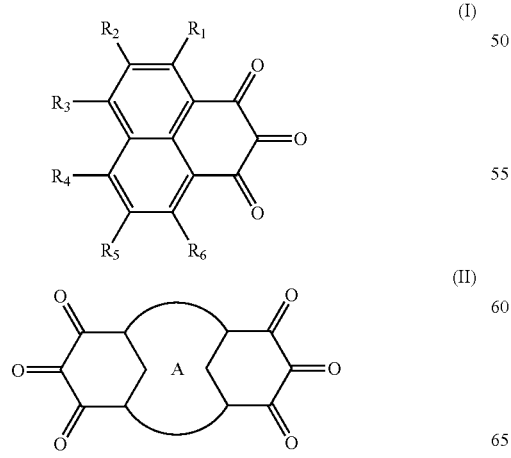

wherein $R^1$, $R^2$, $R^3$, $R^4$, $R^5$ and $R^6$, which may be identical or different, are chosen from hydrogen atoms; halogen radicals; $C_{1-6}$ alkyl radicals; hydroxyl radicals; $C_{1-6}$ alkoxy radicals; optionally substituted benzoxy radicals; optionally substituted aryloxy radicals; amino radicals; mono- and di($C_{1-6}$ alkyl)amino radicals; mono- and di($C_{1-6}$ hydroxy-alkyl)amino radicals; thio radicals; $C_{1-6}$ alkylthio radicals; $C_{1-6}$ thioalkyl radicals; ($C_{1-6}$ alkyl)carbonyl radicals; hydrogenocarbonyl radicals; hydroxycarbonyl radicals; ($C_{1-6}$ alkoxy)carbonyl radicals; nitro radicals; sulphonato radicals; tri($C_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl and pyridinyl radicals;

alternatively, $R^1$ and $R^2$, $R^2$ and $R^3$, $R^3$ and $R^4$, $R^4$ and $R^5$, or $R^5$ and $R^6$ form together, in pairs, an entity chosen from —O—CH$_2$—O— radicals; and aromatic and non-aromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals, and A is chosen from aromatic and aliphatic polycyclic systems optionally comprising at least one heteroatom chosen from N, O, S and P and optionally bearing at least one substituent chosen from halogen atoms, and $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl, and pyridinyl radicals, and at least one second compartment comprising at least one activator that makes it possible to modify the kinetics of the reaction of the at least one polycyclic aromatic vicinal trione of formula (I) or (II) with the keratin material.

17. A process for dyeing hair comprising applying, to the hair, a cosmetic composition for dyeing keratin material comprising, in a cosmetically acceptable medium, at least one agent chosen from non-ionic, cationic, anionic and amphoteric surfactants, and from nonionic, cationic, anionic and amphoteric polymers, and at least one polycyclic aromatic vicinal trione of formula (I) or (II):

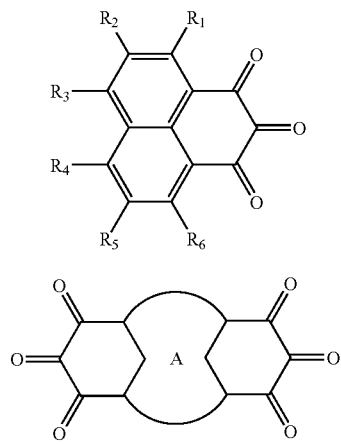

(I)

(II)

wherein
R$^1$, R$^2$, R$^3$, R$^4$, R$^5$ and R$^6$, which may be identical or different, are chosen from hydrogen atoms; halogen radicals; C$_{1-6}$ alkyl radicals; hydroxyl radicals; C$_{1-6}$ alkoxy radicals; optionally substituted benzoxy radicals; optionally substituted aryloxy radicals; amino radicals; mono- and di(C$_{1-6}$ alkyl)amino radicals; mono- and di(C$_{1-6}$ hydroxy-alkyl)amino radicals; thio radicals; C$_{1-6}$ alkylthio radicals; C$_{1-6}$ thioalkyl radicals; (C$_{1-6}$ alkyl)carbonyl radicals; hydrogenocarbonyl radicals; hydroxycarbonyl radicals; (C$_{1-6}$ alkoxy)carbonyl radicals; nitro radicals; sulphonato radicals; tri(C$_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, C$_{1-6}$ alkyl, hydroxyl, C$_{1-6}$ alkoxy, amino, mono- and di(C$_{1-6}$ alkyl) amino, mono- and di(C$_{1-6}$ hydroxyalkyl)amino, thio, C$_{1-6}$ alkylthio, C$_{1-6}$ thioalkyl, (C$_{1-6}$ alkyl)carbonyl, hydrogenocarbonyl, hydroxycarbonyl, (C$_{1-6}$ alkoxy) carbonyl, nitro, sulphonato, tri(C$_{1-6}$ alkyl)ammonio, phenoxy, imidazolyl and pyridinyl radicals;
alternatively, R$^1$ and R$^2$, R$^2$ and R$^3$, R$^3$ and R$^4$, R$^4$ and R$^5$, or R$^5$ and R$^6$ form together, in pairs, an entity chosen from —O—CH$_2$—O— radicals; and aromatic and non-aromatic, 5- and 6-membered rings, optionally comprising at least one heteroatom chosen from N, O, S and P, and optionally bearing at least one substituent chosen from halogen atoms, C$_{1-6}$ alkyl, hydroxyl, C$_{1-6}$ alkoxy, amino, mono- and di(C$_{1-6}$ alkyl)amino, mono- and di(C$_{1-6}$ hydroxyalkyl)amino, thio, C$_{1-6}$ alkylthio, C$_{1-6}$ thioalkyl, (C$_{1-6}$ alkyl)carbonyl, hydrogenocarbonyl, hydroxycarbonyl, (C$_{1-6}$ alkoxy)carbonyl, nitro, sulphonato, tri(C$_{1-6}$ alkyl)ammonio, imidazolyl, and pyridinyl radicals, and
A is chosen from aromatic and aliphatic polycyclic systems optionally comprising at least one heteroatom chosen from N, O, S and P and optionally bearing at least one substituent chosen from halogen atoms, and C$_{1-6}$ alkyl, hydroxyl, C$_{1-6}$ alkoxy, amino, mono- and di(C$_{1-6}$ alkyl)amino, mono- and di(C$_{1-6}$ hydroxyalkyl)amino, thio, C$_{1-6}$ alkylthio, C$_{1-6}$ thioalkyl, (C$_{1-6}$ alkyl)carbonyl, hydrogenocarbonyl, hydroxycarbonyl, (C$_{1-6}$ alkoxy)carbonyl, nitro, sul-phonato, tri(C$_{1-6}$ alkyl)ammonio, phenoxy, imidazolyl, and pyridinyl radicals; and
waiting a sufficient leave-in time to allow the desired color to be obtained, and then rinsing and washing the hair.

18. The process of dyeing hair according to claim 17, further comprising heating the hair impregnated with the composition to a temperature less than or equal to 80° C.

19. The process of dyeing hair according to claim 17, further comprising heating the hair impregnated with the composition to a temperature of less than or equal to 60° C.

20. A process for dyeing hair comprising
applying, to the hair, a multicomponent ready-to-use dyeing composition for keratin material comprising
at least one first component comprising a composition comprising, in a medium appropriate for dyeing, at least one polycyclic aromatic vicinal trione of formula (I) or (II):

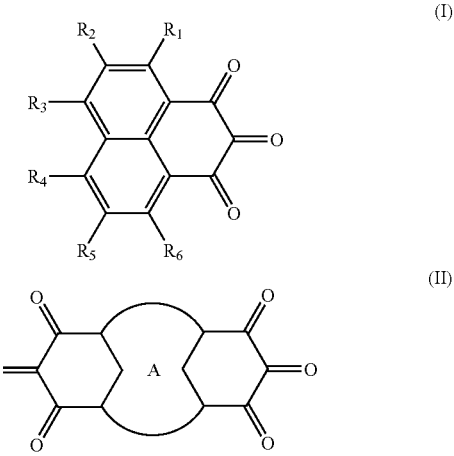

(I)

(II)

wherein
R$^1$, R$^2$, R$^3$, R$^4$, R$^5$ and R$^6$, which may be identical or different, are chosen from hydrogen atoms; halogen radicals; C$_{1-6}$ alkyl radicals; hydroxyl radicals; C$_{1-6}$ alkoxy radicals; optionally substituted benzoxy radicals; optionally substituted aryloxy radicals; amino radicals; mono- and di(C$_{1-6}$ alkyl)amino radicals; mono- and di(C$_{1-6}$ hydroxy-alkyl)amino radicals; thio radicals; C$_{1-6}$ alkylthio radicals; C$_{1-6}$ thioalkyl radicals; (C$_{1-6}$ alkyl)carbonyl radicals; hydrogenocarbonyl radicals; hydroxycarbonyl radicals; (C$_{1-6}$ alkoxy)carbonyl radicals; nitro radicals; sulphonato radicals; tri(C$_{1-6}$ alkyl)ammonio radicals; and aromatic radicals comprising at least 5 members, that are monocyclic or polycyclic, comprising fused or non-fused rings, optionally comprising at least one heteroatom chosen from N, O, S and P, and optionally bearing at least one substituent chosen from halogen atom, C$_{1-6}$ alkyl, hydroxyl, C$_{1-6}$ alkoxy, amino, mono- and di(C$_{1-6}$ alkyl) amino, mono- and di(C$_{1-6}$ hydroxyalkyl)amino, thio, C$_{1-6}$ alkylthio, C$_{1-6}$ thioalkyl, (C$_{1-6}$ alkyl)carbonyl, hydrogenocarbonyl, hydroxycarbonyl, (C$_{1-6}$ alkoxy) carbonyl, nitro, sulphonato, tri(C$_{1-6}$ alkyl)ammonio, phenoxy, imidazolyl and pyridinyl radicals;
alternatively, R$^1$ and R$^2$, R$^2$ and R$^3$, R$^3$ and R$^4$, R$^4$ and R$^5$, or R$^5$ and R$^6$ form together, in pairs, an entity chosen from —O—CH$_2$—O— radicals; and aromatic and non-aromatic, 5- and 6-membered rings, optionally comprising at least one heteroatom chosen from N, O, S and P, and optionally bearing at least one substituent chosen from halogen atoms, $C_{1-6}$ alkyl, hydroxyl, $C_{1-6}$ alkoxy, amino, mono- and di($C_{1-6}$ alkyl)amino, mono- and di($C_{1-6}$ hydroxyalkyl)amino, thio, $C_{1-6}$ alkylthio, $C_{1-6}$ thioalkyl, ($C_{1-6}$ alkyl)carbonyl, hydrogenocarbonyl, hydroxycarbonyl, ($C_{1-6}$ alkoxy)carbonyl, nitro, sulphonato, tri($C_{1-6}$ alkyl)ammonio, imidazolyl, and pyridinyl radicals, and A is chosen from aromatic and aliphatic polycyclic systems optionally comprising at least one heteroatom chosen from N, O, S and P and optionally bearing at least one substituent chosen from halogen atoms, and $C_{1-6}$ alkyl, hydroxyl, $C_{1-6}$ alkoxy, amino, mono- and di($C_{1-6}$ alkyl)amino, mono- and di($C_{1-6}$ hydroxyalkyl) amino, thio, $C_{1-6}$ alkylthio, $C_{1-6}$ thioalkyl, ($C_{1-6}$ alkyl) carbonyl, hydrogenocarbonyl, hydroxycarbonyl, ($C_{1-6}$ alkoxy)carbonyl, nitro, sulphonato, tri($C_{1-6}$ alkyl)ammonio, phenoxy, imidazolyl, and pyridinyl radicals, and at least one second component comprising at least one activator that makes it possible to modify the kinetics of the reaction of the at least one polycyclic aromatic vicinal trione of formula (I) or (II) with the hair;

successively applying, to the hair, in any order, the at least one first component and the least one second component;

waiting a sufficient leave-in time to allow the desired color to be obtained, rinsing and washing the hair.

21. The process of dyeing hair according to claim 20, further comprising an intermediate rinsing step between the application of the at least one first or second component and the application of the at least one first or second component.

22. The process of dyeing hair according to claim 20, comprising heating the hair impregnated with either the at least one first or at least one second component to a temperature of 80° C.

23. The process of dyeing hair according to claim 20, comprising heating the hair impregnated with either the at least one first or at least one second component to a temperature of 60° C.

* * * * *